(12) United States Patent
Milczarek et al.

(10) Patent No.: US 10,532,022 B2
(45) Date of Patent: Jan. 14, 2020

(54) WHOLE STABLIZED OLIVE MILL PROCESS WATER, PRODUCTION THEREOF AND USES THEREOF

(71) Applicants: The United States of America, as represented by the Secretary of Agriculture, Washington, DC (US); McEvoy of Marin, LLC, Petaluma, CA (US)

(72) Inventors: Rebecca R Milczarek, Albany, CA (US); Jeffrey A Creque, Petaluma, CA (US); John Bailey, Ukiah, CA (US); Ellen Roggemann, Petaluma, CA (US)

(73) Assignees: The United States of America, as represented by The Secretary of Agriculture, Washington, DC (US); McEvoy of Marin, LLC, Petaluma, CA (US)

(*) Notice: Subject to any disclaimer, the term of this patent is extended or adjusted under 35 U.S.C. 154(b) by 870 days.

(21) Appl. No.: 14/804,082

(22) Filed: Jul. 20, 2015

(65) Prior Publication Data
US 2016/0015626 A1    Jan. 21, 2016

Related U.S. Application Data

(60) Provisional application No. 62/027,015, filed on Jul. 21, 2014.

(51) Int. Cl.
*A61K 36/63* (2006.01)
*A61K 8/97* (2017.01)
*A61Q 19/00* (2006.01)
*A61Q 19/10* (2006.01)
*A23L 2/52* (2006.01)

(52) U.S. Cl.
CPC ........ *A61K 8/97* (2013.01); *A23L 2/52* (2013.01); *A61Q 19/00* (2013.01); *A61Q 19/10* (2013.01)

(58) Field of Classification Search
CPC ..................................................... A61K 36/63
USPC .......................................................... 424/777
See application file for complete search history.

(56) References Cited

U.S. PATENT DOCUMENTS

| | | | | |
|---|---|---|---|---|
| 6,165,475 A * | 12/2000 | Crea | ............... | A23L 33/105 424/769 |
| 7,713,569 B2 * | 5/2010 | Crea | ............... | A01N 31/16 424/769 |
| 8,236,993 B2 * | 8/2012 | Lopez Mas | ......... | B01J 19/18 426/431 |
| 2005/0103711 A1 * | 5/2005 | Emmons | ............. | A23L 33/105 210/639 |
| 2008/0207480 A1 * | 8/2008 | Pipko | .............. | C11D 9/045 510/491 |

* cited by examiner

*Primary Examiner* — Michael Barker
*Assistant Examiner* — Deborah A Davis
(74) *Attorney, Agent, or Firm* — John D. Fado; Robert D. Jones

(57) ABSTRACT

The present invention relates to processes for producing treated olive mill process water (OMPW). In some exemplary embodiments, the treated OMPW is used in the preparation/production of body care products.

3 Claims, 12 Drawing Sheets

US 10,532,022 B2

WHOLE STABLIZED OLIVE MILL PROCESS WATER, PRODUCTION THEREOF AND USES THEREOF

FIELD OF THE INVENTION

Embodiments of the invention relate to processes for producing treated olive mill process water (OMPW). In some exemplary embodiments, the treated OMPW is used in the preparation/production of body care products and food products.

BACKGROUND OF THE INVENTION

Olive mill process water (OMPW) is a by-product of the olive milling process for producing olive oil. OMPW may be produced from either a 3-phase olive mill process or a 2-phase olive mill process. In 3-phase olive milling, crushed olives and pure water are combined and subjected to centrifugation. The process results in 3 process streams: olive oil, a damp solid mass called "pomace", and a watery stream called "olive mill process water" (OMPW). In 2-phase olive milling, crushed olives are subjected to centrifugation without adding additional water. Either process results in 3 process streams: olive oil, a damp solid mass called "pomace", and a watery stream called "olive mill process water" (OMPW) Alternative names for OMPW include "olive mill waste water" and "vegetation water". Although the express purpose of olive milling is the production of olive oil, OMPW is a secondary product of the milling process.

Unfortunately, OMPW represents a cost to olive mills because the olive mills must pay to have the OMPW removed and treated in municipal waste treatment plants. Alternatively, OMPW is used as a low value soil amendment for olive orchards. However, even as a soil amendment, OMPW must be used carefully and sparingly, so as to avoid the risk of river and ecosystem pollution. Because large quantities of OMPW are generated in the olive oil production process, the disposal of OMPW presents a problem for olive oil producers.

Thus, there exists a need in the art for improved disposal methods and increased usages for OMPW. Fortunately, as will be clear from the following disclosure, the present invention provides for this and other needs.

SUMMARY OF THE INVENTION

In one aspect, the disclosure provides a process for producing treated olive mill process water (OMPW) having antioxidant level that is increased by comparison to untreated OMPW. In an exemplary embodiment, the disclosure provides a method for preparing treated olive mill process water (treated OMPW) from olive mill process water (OMPW), wherein the treated OMPW has increased antioxidant levels by comparison to the OMPW, the method comprising: (i) ramping up temperature of the OMPW from a starting temperature to a target temperature, wherein the target temperature is in a range that is between about 70° C. and about 138° C.; (ii) holding the OMPW at the target temperature, for a target time, and (iii) cooling the OMPW rapidly to room temperature, thereby preparing treated OMPW from OMPW, wherein the treated OMPW has increased antioxidant levels by comparison to the OMPW. In an exemplary embodiment, the ramping up is from a starting temperature of ambient temperature (20° C.), the target temperature is 135° C., the target time is 2 seconds, and cooling is to ambient temperature in 15 minutes or less. In another exemplary embodiment, the ramping up is from a starting temperature of ambient temperature (20° C.), the target temperature is 100° C., the target time is 1 second, and the cooling is to ambient temperature in 15 minutes or less. In another exemplary embodiment, the ramping up is from a starting temperature of ambient temperature (20° C.), the target temperature is 72° C., the target time is 15 seconds, and the cooling is to ambient temperature in 15 minutes or less. In one exemplary embodiment, the antioxidant levels of the treated OMPW is increased by at least about 5% by comparison to the untreated OMPW. In one exemplary embodiment, the method further comprises step (iv) homogenizing the treated OMPW.

In one aspect, the disclosure provides treated OMPW made according to the method disclosed herein.

In one aspect, the disclosure provides a personal care product comprising treated OMPW. In one exemplary embodiment, the personal care product is a member selected from the group consisting of: a liquid soap, a bar soap, a skin toner, a lotion, and a cream. In another exemplary embodiment, the personal care product is a member selected from the group consisting of a skin toner and a serum and the personal care product comprises treated OMPW in a concentration that is in a range of between about 3% and about 7%. In another exemplary embodiment, the personal care product is a glycerin bar soap and the glycerin bar soap comprises treated OMPW in a concentration that is in a range of between about 5% and about 15%.

In another aspect, the disclosure provides a food product comprising treated OMPW. In one exemplary embodiment, the food product is a member selected from the group consisting of: a beverage and a salad dressing.

Other features, objects and advantages of the invention will be apparent from the detailed description which follows.

DETAILED DESCRIPTION OF THE INVENTION

Definitions

Figure 1:
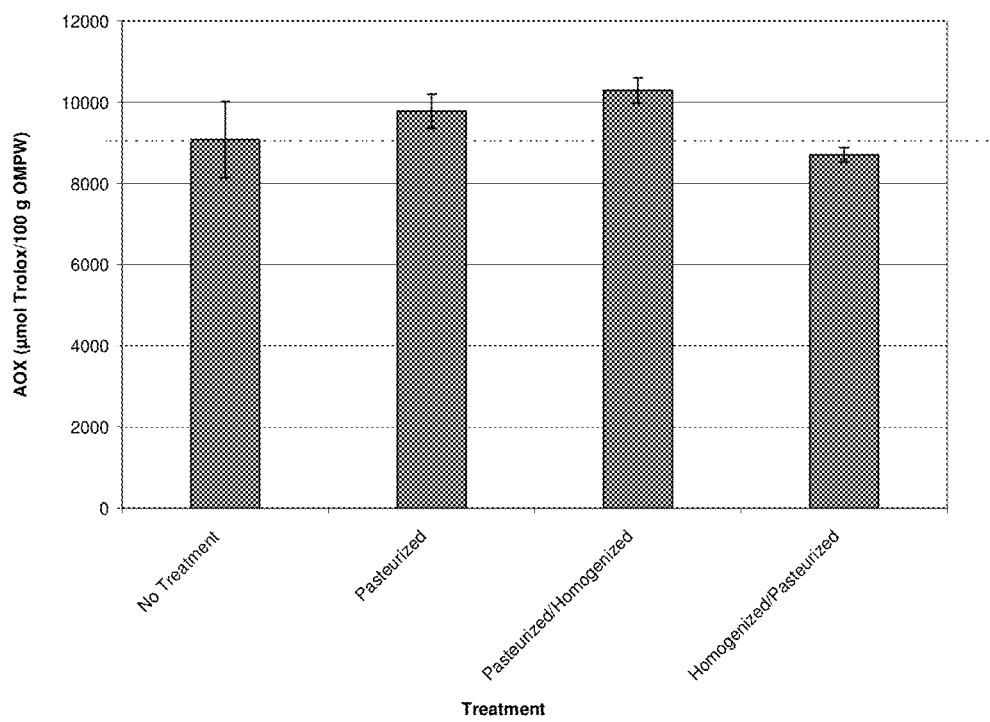
FIG. 1 illustrates the antioxidant (AOX) levels in OMPW samples that have been subjected to various combinations of heat treatment (pasteurization) and homogenization as disclosed in Example 1. Vertical brackets represent ±1 standard deviation of 3 replicate measurements for each data point. The dashed line indicates the AOX of the No Treatment samples, for visual reference. The Pasteurized and Pasteurized/Homogenized samples exhibited AOX increases of 7.7% and 13.3%, respectively, over the No Treatment sample, but the Homogenized/Pasteurized sample exhibited a 4.2% AOX decrease below the No Treatment sample.

The expression "olive mill process water" (OMPW) "olive mill waste water" "vegetation water" as used herein refers to the aqueous stream of the olive milling process. In one exemplary embodiment OMPW is produced in a 2-phase olive milling process. In another exemplary embodiment, OMPW is produced in a 3-phase olive milling process.

The term "heat treatment" "thermal treatment" or "pasteurization" are used interchangeably herein. The term "thermal treatment" as used herein refers to a process of heating OMPW to a specific temperature for a defined length of time and then immediately cooling it after it is removed from the heat.

The expression "target temperature" as used herein refers to a temperature selected for thermal treatment of OMPW.

The expression "cooling the OMPW rapidly to room temperature" as used herein, refers to active cooling of the treated OMPW in order to halt the heat treatment process.

Typically, "active cooling" utilizes an input of energy to cool a substance e.g., OMPW, to a temperature below the temperature of the heat treatment, thereby causing termination of the heat treatment as fast as possible. In some exemplary embodiments, "active cooling" includes conductive and radiative cooling mechanisms that require electricity from an external source to operate. Exemplary active cooling systems include e.g., actively pumped refrigerant systems, thermoelectric systems, active heat pump systems, active vapor-compression refrigeration systems, active heat exchanger systems, etc.

The term "treated olive mill process water" or "treated OMPW" as used herein, refers to heat treated or pasteurized OMPW. In some exemplary embodiments, "treated OMPW" is further processed by homogenization.

The term "homogenize" or "homogenization" as used herein, refers to any process suitable for breaking up particles in treated OMPW thereby to reducing or eliminating settling of the solid components and providing a uniform mixture having uniform in consistency.

The term "body care product" as used herein, refers to products useful for personal hygiene and cosmetics such as e.g., soaps, shampoos, toners, lotions, creams, lip balm, lipstick, body oils, body gels, treatment creams, skin protection ointments, suntan/sun block lotion, moisturizing gels, moisturizing sprays, revitalizing body sprays, cellulite gels, peeling preparations, shaving preparations, etc.

I. Introduction:

In an exemplary embodiment, the invention provides a process for producing a treated olive mill process water (treated OMPW) having increased antioxidant levels by comparison to untreated olive mill process water (OMPW). In some embodiments, treated OMPW has a reduced microbial load by comparison to untreated OMPW. Treated OMPW is useful inter alia as an ingredient in soaps and body care products.

II. Production of Whole Stabilized Olive Mill Process Water (Treated OMPW)

A. Generation of Olive Mill Process Water (OMPW)

Olive mill process water (OMPW), sometimes referred to as "vegetation water", is an aqueous by-product stream that results from the extraction of olive oil from crushed olives. Typically, OMPW is produced from pitted or unpitted olive pulp. The olives may be either conventionally or organically grown. In general, olives are first pressed, centrifuged, or otherwise mechanically treated to obtain a liquid-phase mixture including olive oil, OMPW, and solid by-products. Thereafter, the OMPW is separated from the rest of the liquid phase mixture and collected. Exemplary methods of obtaining OMPW are described e.g., in U.S. Pat. Nos. 6,165,475 and 6,197,308.

For purposes of commercial production, it may be desirable to automate various aspects of the process. In this regard, one embodiment contemplates the use of an apparatus as disclosed e.g., in U.S. Pat. Nos. 4,452,744, 4,522,119, and 4,370,274. Thus, in an exemplary embodiment, olives are fed to a pulper that separates the olive pits from the olives to obtain a pitless olive meat. The meat is then taken up by an extraction screw that subjects the meat to an extraction pressure sufficient to withdraw a liquid phase, comprising oil, water, and a minor proportion of olive pulp. The liquid phase is collected in a bin and then sent to a clarifying centrifuge that separates the pulp from the liquid phase to obtain a mixture comprising olive oil and OMPW. A purifying centrifuge then separates the OMPW and a small proportion of solid matter from the mixture to obtain an olive oil, substantially free of OMPW that is collected in a tank. The OMPW is collected and processed as disclosed herein for use as an ingredient in body care products.

After production, OMPW may be stored under freezing or refrigeration conditions until further processing can be performed. Initial storage at freezing or refrigeration temperature inhibits mold growth before additional processing can take place. If the OMPW is frozen, it should be thawed completely before further processing.

B. Processing of OMPW

I. Thermal Treatment (Pasteurization)

Thermal treatment (Pasteurization) is typically carried out as a first processing step. In addition to killing mold spores and thereby stabilizing the OMPW for storage, thermal treatment increases the antioxidant levels of OMPW. In some exemplary embodiments, pasteurization alone increases antioxidant levels of OMPW. In other exemplary embodiments, pasteurization followed by homogenization increases the antioxidant levels of OMPW. When OMPW or treated OMPW is subjected to homogenization, the OMPW is typically subjected to thermal treatment before homogenization.

Without being bound by theory, it is believed that in addition to killing microbes and thereby extending the shelf life, thermal treatment releases compounds (from the olive tissue cells) that only exhibit antioxidant activity if they are free-floating and additionally heat treatment inactivates enzymes naturally present in the OMPW that would break down these compounds. Subsequent homogenization releases even more of the compounds.

Thus, without being bound by theory it is further believed that if the OMPW is homogenized before heat treatment, the antioxidant compounds are released but then are very quickly degraded by the enzymes.

In general, the temperature/time combinations useful for stabilizing OMPW and increasing antioxidant levels are similar to typical dairy pasteurization conditions (see e.g., Tetra Pak. Dairy Processing Handbook. 1995. Tetra Pak Processing Systems AB, Lund, Sweden; Hall, C. W., and G. M. Trout. Milk Pasteurization. 1968. AVI Publ. Co., Inc., Wesport, Conn.). Thus, in exemplary embodiments, thermal treatment comprises heating the OMPW to a target temperature and holding the heated OMPW at the target temperature for a set amount of time thereby providing thermally treated OMPW. After heating to the target temperature and holding for the set amount of time, the thermally treated OMPW is rapidly cooled to ambient temperature (about 20° C.). Exemplary target temperatures held for a set amount of time include, but are not limited to: 63° C. (145° F.) 30 minutes; 72° C. (161° F.) 15 seconds; 89° C. (191° F.) 1.0 second; 90° C. (194° F.) 0.5 seconds; 94° C. (201° F.) 0.1 seconds; 96° C. (204° F.) 0.05 seconds; 100° C. (212° F.) 0.01 seconds, etc.

Cooling the thermally treated OMPW is carried out rapidly in order to stop the thermal treatment. Thus, typically, convective cooling is used to cool thermally treated OMPW. Thus, in an exemplary embodiment, a small benchtop batch is cooled by water running over the vessel to bring the treated OMPW back to ambient temperature in 15 minutes or less. In other exemplary embodiments, an active cooling process is used to cool pilot-scale batches of treated OMPW to ambient temperature in approximately 2 minutes.

To commence thermal treatment of OMPW, a target temperature is typically selected by choosing a temperature that is sufficient to kill most mold spores and microorganisms, but which is not so high as to cook the OMPW. Typically a target temperature is a temperature that is in a range that is between about 70° C. and about 200° C. Thus, in exemplary embodiments, the target temperature is about 70° C., about 75° C., about 80° C., about 85° C., about 90° C., about 95° C., about 100° C., about 105° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., v about 190° C., about 195° C., about 200° C.

Thus, in an exemplary embodiment, thermal treatment comprises heating OMPW from ambient temperature to 135° C. in 60 seconds or less, holding the OMPW at 135° C. for 2 seconds, and then cooling the OMPW to ambient temperature in 15 minutes or less. In another exemplary embodiment, thermal treatment comprises heating OMPW from ambient temperature to 100° C., holding the OMPW at 100° C. for 1 second and then cooling the OMPW to ambient temperature in 15 minutes or less. In still another exemplary embodiment, thermal treatment comprises heating OMPW from ambient temperature to 72° C., holding the OMPW at 72° C. for 15 seconds, and then cooling the OMPW to ambient temperature in 15 minutes or less. Other temperature and hold time combinations sufficient to inactivate mold spores may be used and will be readily apparent to a person of ordinary skill in the art having access to this disclosure and the knowledge in the art.

Thermal treatment (pasteurization) is carried out as a batch or a continuous process. In an exemplary embodiment, a vat pasteurizer comprising a temperature-controlled, closed vat is used for thermal treatment. In this embodiment OMPW is pumped into the vat, the OMPW is heated to the appropriate temperature and held at that temperature for the appropriate time and then cooled. The cooled treated OMPW is then pumped out of the vat. In other exemplary embodiment batch pasteurization is used for thermal treatment of OMPW. In another exemplary embodiment, thermal treatment is carried out in a continuous process. In these embodiments OMPW is pumped through electrically-heated piping zones, and the flow rate of the OMPW is controlled so as to hold the OMPW at the target temperature for the appropriate time. The OMPW is then cooled by flowing into a piping zone that is surrounded by chilled water.

In general, thermal treatment typically increases the antioxidant levels of the OMPW by between about 5% to about 40% or more above the level found in the starting material. In some exemplary embodiments, thermal treatment typically increases the antioxidant levels of the OMPW by about 5%, about 10%, about 15%, about 20%, about 25%, about 30%, about 35%, about 40%, about 45%, above the level found in the starting material.

The particular temperature and hold time combination used during the thermal treatment influences the level of antioxidant levels of the thermally treated OMPW. The particular time temperature combination required to achieve any particular result will be readily apparent to a person having ordinary skill in the art and access to this disclosure.

2. Homogenization

In some exemplary embodiments, after thermal treatment, the thermally-treated OMPW is subjected to a homogenization step. Homogenization is carried out by any method known in the art e.g., blending. In one exemplary embodiment, homogenization comprises blending 500 mL of OMPW for 15 minutes using an immersed, shielded impeller spinning at 10,000 rotations per minute. As the homogenization process generates heat, in exemplary embodiments the vessel holding the OMPW for homogenization is jacketed with a cooling medium so that the OMPW remains at or below ambient temperature during homogenization. In one embodiment, the cooling medium is ice. Other homogenization devices and conditions, which are known to those of skill in the art, may be used.

C. Storage of Treated OMPW

Once the OMPW has undergone thermal treatment or thermal treatment and homogenization, it can be stored in sterilized containers at ambient temperature, refrigerated or frozen. Depending on the particular temperature and hold time combination used during the thermal treatment, the OMPW can be stored from 4 to 12 weeks at ambient without developing visible mold growth.

III. Measuring Antioxidant levels

Antioxidant levels can be measured by any method known in the art. In an exemplary embodiment, antioxidant levels are measured according to methods disclosed in e.g., Brand-Williams et al. ((1995) Lebensm. Wiss. Tech. 28:25-30. However, any suitable method may be used (See e.g., Re § at Apak et al. (2013) Pure Appl. Chem., Vol. 85, No. 5, pp. 957-998).

IV. Incorporation of OMPW into Cosmetic or Dermatological Products

In exemplary embodiments, treated OMPW is used to prepare soaps and body care products. Treated OMPW (both the thermally-treated and thermally treated-homogenized OMPW) are used in place of water in cosmetic or dermatological body products. Exemplary body products include but are not limited to lotions, creams, liquid cleansers, toners and solid bar soaps. Methods for the preparation of dermatological and cosmetic products is well known in the art Created using industry standard method see e.g., M. L. Schlossman (2009) Chemistry and Manufacture of Cosmetics: Volume II—Formulating, 4th Edition, Allured Pub Corp; Anthony Dweck (2010) Formulating Natural Cosmetics, Allured Pub Corp; André O. Barel, Marc Paye, and Howard I. Maibach (2014) Handbook of Cosmetic Science and Technology, CRC Press; S. K. Singh (2010) Handbook on Cosmetics (Processes, Formulae with Testing Methods) Asia, Pacific Business Press Inc.

Cosmetic and dermatological products typically include water as a main ingredient; accordingly the thermally-treated and thermally treated-homogenized OMPW is substituted for water in these products in a ratio from 0% to 100%. The amount of treated OMPW used is typically chosen with an eye to the desired sensory properties, coloration, desired final antioxidant concentration, etc. In an exemplary embodiment, treated OMPW is substituted for water in the formulation disclosed in U.S. Pat. No. 7,214,391. In other exemplary embodiments, treated OMPW is substituted for water in the formulation disclosed in U.S. Pat. No. 4,491,539.

In some exemplary embodiments, treated OMPW is used to prepare a skin toner. Typically, in skin toners, treated OMPW is present in a concentration that is in a range that is between about 3% to about 7%. Thus, in exemplary embodiments, treated OMPW is present in a skin cream formulation at a concentration of 3%. In other exemplary embodiments treated OMPW is present in skin care formulations at a concentration of 4%, 5%, 6% or 7%.

In some exemplary embodiments, treated OMPW is used to prepare a skin cream. Typically, in skin cream treated OMPW is present in a concentration that is in a range that is between about 3% to about 7%. Thus, in exemplary embodiments, treated OMPW is present in a skin cream formulation at a concentration of 3%. In other exemplary embodiments treated OMPW is present in skin care formulations at a concentration of 4%, 5%, 6% or 7%. Typically, when choosing the amount of treated OMPW in a skin cream or other formulation, a person having skill in the art will consider the amount of anti oxidant increase as well as coloration and other factors.

In some exemplary embodiments, treated OMPW is used to prepare facial masque. Typically, in facial masque formulations treated OMPW is present in a concentration that is in a range that is between about 3% to about 10%. Thus, in exemplary embodiments, treated OMPW is present in a facial masque formulation at a concentration of 3%. In other exemplary embodiments treated OMPW is present in skin care formulations at a concentration of about 4%, 5%, 6%, 7%, 8%, 9% or 10%.

Exemplary compositions comprising treated OMPW are suitable for use on all surfaces of the body including the face, hands, head and feet. Thus, in some embodiments, the composition comprising treated OMPW further comprises a cleanser. The resulting body care product will thus be in any form suitable for application to, and cleansing of, the skin. In some exemplary embodiments, the cleanser comprising treated OMPW is in the form of a bar soap. In other exemplary embodiments, the composition comprising treated OMPW and a cleanser is used effectively to clean and/or moisturize other areas of the body, for example, hair on a user's head. In this aspect, the cleanser may be in any form suitable for application to, and cleansing of, the hair. In other embodiments, the composition is in the form of a lotion which is applied to and massaged it into the skin. In still other embodiments, the composition is in the form of a toner which is applied to the skin.

V. Incorporation of OMPW into Food and Beverage Products

In exemplary embodiments, treated OMPW is used to prepare food and beverage products. Treated OMPW (both the thermally-treated and thermally treated-homogenized OMPW) are used in place of water in food and beverage products. Exemplary food products include but are not limited to beverages such as e.g., sport drinks, smoothies and formulations that improve skin quality. Food products further include salad dressings, yogurt, soups, gravies, pasta sauces, etc.

All of the aforementioned food products typically include water as a main ingredient; accordingly the thermally-treated and thermally treated-homogenized OMPW is substituted for water in these products in a ratio from 0% to 100%. In an exemplary embodiment, treated OMPW is substituted for water in the formulation disclosed in U.S. Pat. No. 4,701,338. In other exemplary embodiments, treated OMPW is substituted for water in the formulation disclosed in U.S. Pat. No. 8,337,928.

The following examples are offered to illustrate, but not to limit the invention.

EXAMPLES

Example 1

The following example illustrates an exemplary process by which the antioxidant levels (AOX) of olive mill process water (OMPW) is increased by both a heat treatment and a sequence of heat treatment and homogenization.

OMPW was collected during olive oil production and stored at −20° C. for 3 months. The OMPW was thawed at 2° C. (refrigeration conditions) for 2 weeks and brought to room temperature (about 20° C.) just before heat treatment. A 500 mL aliquot of OMPW was heated in a 1000 mL borosilicate glass beaker in a domestic microwave oven (Panasonic, 1300W) equipped with a fiber optic temperature measurement system (FISO Technologies). The heat treatment sequence was as follows: 100% microwave power for 3 minutes and 30 seconds, 10% microwave power for 30 seconds, remove from microwave oven, cool to room temperature by flowing cold (about 18° C.) running water around the beaker. This heating sequence was determined via preliminary experiments to be sufficient to bring the OMPW to 72° C. for 15 seconds. The OMPW so treated is hereafter referred to as the "Pasteurized" sample. A subset of "Pasteurized" OMPW was further treated by homogenization. Homogenization was performed by using a laboratory homogenizer operating at 10,000 RPM. About 150 mL of previously-thermally treated OMPW were homogenized for 10 minutes under these conditions. The OMPW so treated is hereafter referred to as the "Pasteurized/Homogenized" sample. A subsample of the OMPW was subjected to homogenization, as described above, before pasteurization, also as described above; the OMPW so treated is hereafter referred to as the "Homogenized/Pasteurized" sample. A subsample of the OMPW was not subjected to any heat treatment or homogenization; this OMPW is hereafter referred to as the "No Treatment" sample.

The AOX of the four samples ("No Treatment", "Pasteurized", "Pasteurized/Homogenized", and "Homogenized/Pasteurized") was measured using a modified version of the method described by Brand-Williams et al. ((1995) Lebensm. Wiss. Tech. 28:25-30). Briefly, 1 mL of OMPW was mixed with 19 mL of methanol. A total of 25 µL of this mixture (equivalent methanol volume as control) was added to 2975 µL of 2,2-diphenyl-1-picrylhydrazyl (103.2 µM in methanol, absorbance of approximately 1.2 at 515 nm) in a covered shaker at room temperature. Absorbance readings of the samples were taken at 515 nm using a spectrophotometer (SHIMADZU Scientific Instruments, Inc.). The mixture was allowed to react until steady state conditions were reached (no significant decrease in absorbance was experienced as compared to the control—approximately 20 to 22 h). The AOX was calculated by measuring the difference in absorbance of samples as compared to the control sample, expressed as percentage inhibition:

Inhibition, %=(1−Abs_sample/Abs_control)*100 where Abs_sample and Abs_control are, respectively, absorbance with and without sample extract. AOX was expressed as µmol Trolox equivalents/100 g OMPW.

The color of the four samples was measured using a tristimulus colorimeter (Minolta). The lightness of the samples was measured using the L* color component, which has no units. An L* value of 0 indicates a completely dark (black) sample, while an L* value of 100 represents a completely bright (white) sample.

Figure 2:
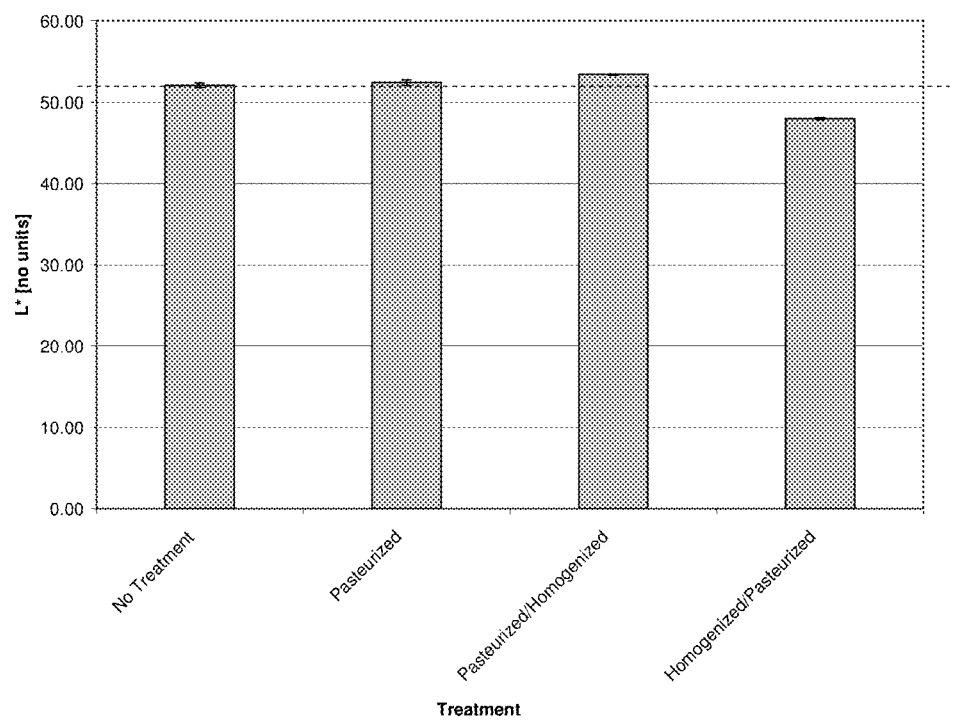
FIG. 2 illustrates the color results of these procedures. Vertical brackets represent ±1 standard deviation of 3 replicate measurements for each data point. The dashed line indicates the L* color value of the No Treatment samples, for visual reference. The Pasteurized and Pasteurized/Homogenized samples maintained the lightness of the No Treatment sample, but the Homogenized/Pasteurized sample darkened considerably.

FIG. 1 illustrates the AOX results of these procedures. In FIG. 1 and FIG. 2, vertical brackets represent ±1 standard deviation of 3 replicate measurements for each data point. The dashed line indicates the AOX of the No Treatment samples, for visual reference. The Pasteurized and Pasteurized/Homogenized samples exhibited AOX increases of 7.7% and 13.3%, respectively, over the No Treatment sample, but the Homogenized/Pasteurized sample exhibited a 4.2% AOX decrease below the No Treatment sample.

FIG. 2 illustrates the color results of these procedures. The dashed line indicates the L* color value of the No Treatment samples, for visual reference. The Pasteurized and Pasteurized/Homogenized samples maintained the lightness of the No Treatment sample, but the Homogenized/Pasteurized sample darkened considerably.

Example 2

The following example illustrates an exemplary process by which the AOX of OMPW is increased by both a heat treatment and a sequence of heat treatment and homogenization, and this increase was maintained in the heat-treated material during 6 weeks of refrigerated storage.

OMPW was prepared according to the methods of Example 1, with the exception that the thawed OMPW was held at 2° C. for 4 weeks (vs. 2 weeks in Example 1) before heat treatment and homogenization. Furthermore, a subsample of OMPW was homogenized by the method in Example 1 with no heat treatment before or after homogenization; this OMPW is hereafter referred to as the "Homogenized" sample. AOX of all 5 samples ("No Treatment", "Pasteurized", "Pasteurized/Homogenized", "Homogenized/Pasteurized", and "Homogenized") was measured according to the method of Example 1. AOX was measured the same day that the heat treatment and homogenization were performed as well as 4 weeks and 6 weeks after that day. All treated samples were held at 2° C. between AOX measurements.

Figure 3:
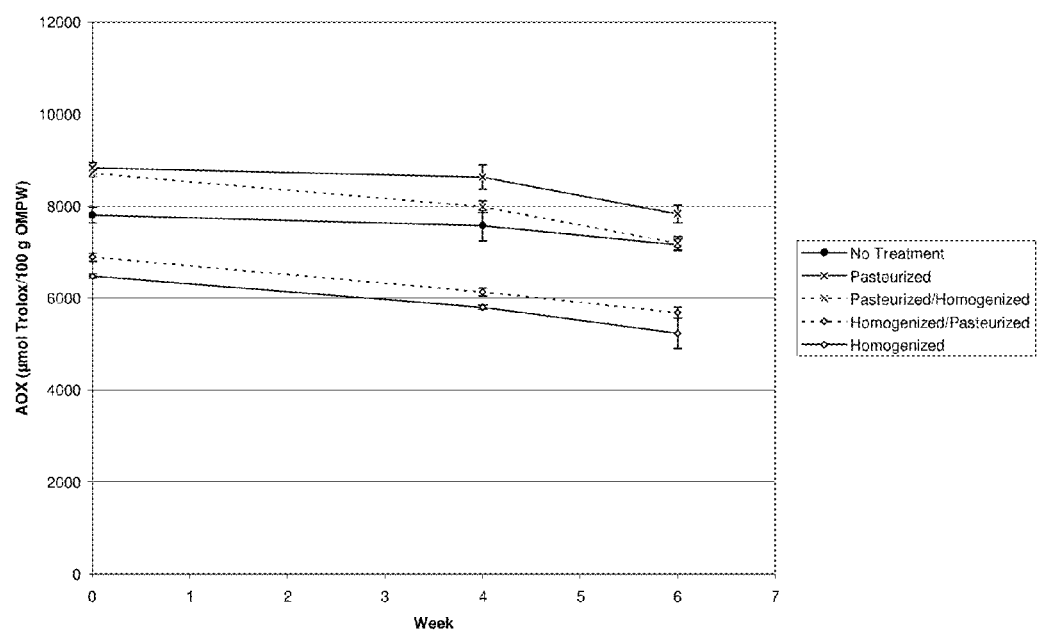
FIG. 3 illustrates the antioxidant (AOX) levels in OMPW samples that have been subjected to various combinations of heat treatment (pasteurization) and homogenization as disclosed in Example 2. OMPW was prepared according to the methods of Example 1, with the exception that the thawed OMPW was held at 2° C. for 4 weeks before heat treatment and homogenization. A subsample of OMPW was homogenized with no heat treatment before or after homogenization; this OMPW is referred to as the "Homogenized" sample. AOX of all 5 samples ("No Treatment", "Pasteurized", "Pasteurized/Homogenized", "Homogenized/Pasteurized", and "Homogenized") was measured the same day that the heat treatment and homogenization were performed as well as 4 weeks and 6 weeks after that day. All treated samples were held at 2° C. between AOX measurements. As can be seen in FIG. 3, at Week 0 the Pasteurized and Pasteurized/Homogenized samples exhibited AOX increases of 13.1% and 11.6%, respectively, over the No Treatment sample. In contrast, at Week 0, the Homogenized/Pasteurized and Homogenized samples exhibited AOX decreases of 11.7% and 16.7%, respectively, below the No Treatment sample. The relative AOX levels among the samples persisted through 4 weeks and 6 weeks of refrigerated storage.

The results of these procedures are shown in FIG. 3. At Week 0 (i.e. immediately after heat treatment and homogenization), the Pasteurized and Pasteurized/Homogenized samples exhibited AOX increases of 13.1% and 11.6%, respectively, over the No Treatment sample. In contrast, at Week 0, the Homogenized/Pasteurized and Homogenized samples exhibited AOX decreases of 11.7% and 16.7%, respectively, below the No Treatment sample. The relative AOX levels among the samples persisted through 4 weeks and 6 weeks of refrigerated storage, with the exception that the Pasteurized/Homogenized sample gradually decreased in AOX until it reached parity with the No Treatment sample at Week 6. In FIG. 3, vertical brackets represent ±1 standard deviation of 3 replicate measurements for each data point.

Example 3

The following example illustrates an exemplary process by which the AOX of OMPW is increased by heat treatments at multiple pasteurization temperatures.

OMPW was prepared according to the methods of Example 1, with the exception that homogenization at 10,000 RPM for 15 minutes was performed on all samples after heat treatment, making all heat-treated samples similar to the "Pasteurized/Homogenized" samples of Examples 1 and 2. The target heat treatment temperatures and times were as follows: 72° C. for 15 seconds, 100° C. for 1 second, and 138° C. for 2 seconds. In this Example, the heat treatments were applied to 20 mL aliquots of OMPW in closed vessels in a laboratory microwave heating system (Milestone Ethos EX). Using a temperature feedback system, the microwave heating system automatically and continuously adjusts the applied power to heat the sample according to a preset sequence. The heating sequence was as follows: ramp from room temperature (about 20° C.) to target temperature in 2 minutes, then hold at target temperature for target time. Immediately after heating, the samples were removed from the microwave heating system and cooled to room temperature by placing the closed vessels under cold (about 18° C.) running water for 20 minutes. Homogenization was performed on the samples after they reached room temperature. The "No Treatment" sample did not receive any heat treatment but was homogenized in the same way as the 72° C., 100° C., and 138° C. samples.

Figure 4:
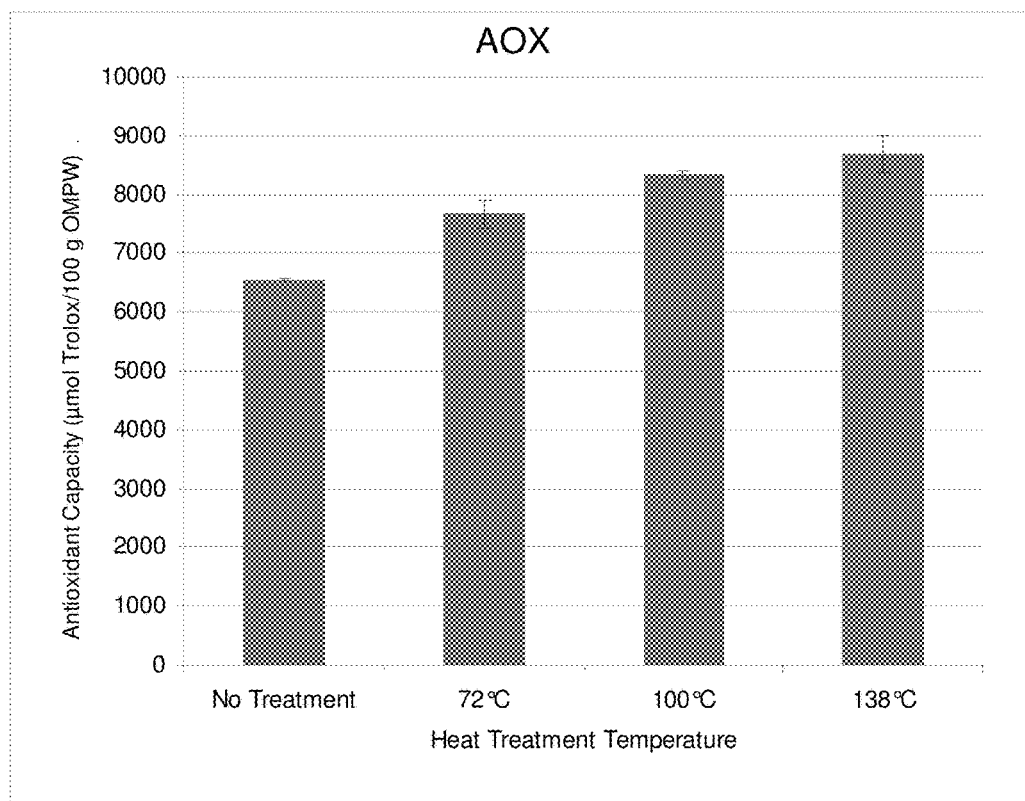
FIG. 4. illustrates the increased antioxidant levels (AOX) of OMPW following heat treatments at multiple common pasteurization temperatures as disclosed I Example 3. The target heat treatment temperatures and times were as follows: 72° C. for 15 seconds, 100° C. for 1 second, and 138° C. for 2 seconds. Vertical brackets represent ±1 standard deviation of 3 replicate measurements for each data point. The 72° C., 100° C., and 138° C. samples exhibited AOX increases of 18.7%, 30.6%, and 36.2%, respectively, over the No Treatment sample.

The results of these procedures are shown in FIG. 4. In FIG. 4, vertical brackets represent ±1 standard deviation of 3 replicate measurements for each data point. The 72° C., 100° C., and 138° C. samples exhibited AOX increases of 18.7%, 30.6%, and 36.2%, respectively, over the No Treatment sample.

Example 4

The following example illustrates the long-term stability of the treated OMPW under both refrigeration and ambient temperature conditions.

From August 2013 to November 2013, we performed a shelf-life experiment ("Shelf Life Study #1") testing 2 different thermal treatments (plus 1 control) and 2 storage conditions. The dependent variables of this experiment are summarized below.
Processing Methods
  No Heat Treatment (control)
  High Temperature Short Time (HTST: 72° C. for 15 seconds)
  Ultra Pasteurization (UP: 100° C. for 1 second)
  Storage Conditions
  Ambient (~20° C., laboratory room temperature)
  Refrigeration (2° C.)

Figure 5:
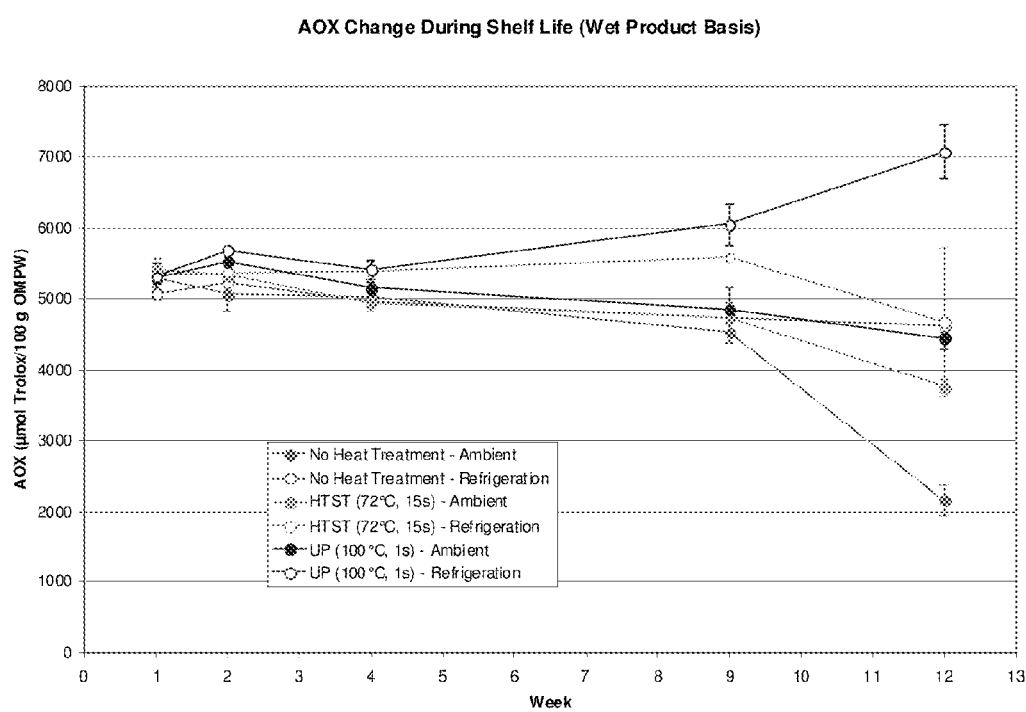
FIG. 5. Shows AOX changes over time for Shelf Life Study #1.

All samples were subjected to thermal treatment before homogenization. Also, all samples were frozen upon collection in November 2011 and thawed out for 2 weeks before processing. Quality measurements were made at Weeks 0, 2, 4, 9, and 12. Findings from Shelf Life Study #1 were as follows:

Among the OMPW samples, AOX diverged during the storage time, with some samples increasing in AOX, some decreasing, and some remaining steady. This is illustrated in FIG. 5. In FIG. 5, vertical brackets represent ±1 standard deviation of 3 replicate measurements for each data point From FIG. 5, one can see that the samples stored under refrigeration (open dots) generally fared better than their ambient-stored counterparts (opaque dots). Further, by the end of the study, at a given storage condition, the order of AOX was UP>HTST>control. This indicates that the thermal treatments we applied to OMPW preserve or enhance AOX of this material, compared to an untreated control.

The a* color value measures the green-red color of a sample (low a* corresponds to a more green sample, high a* corresponds to a more red sample); in OMPW, a higher a* value indicates more browning of the material, which is undesirable. In Shelf Life Study #1, we found that a* value varies among the samples and over storage time as indicated in FIG. 6.

Figure 6:
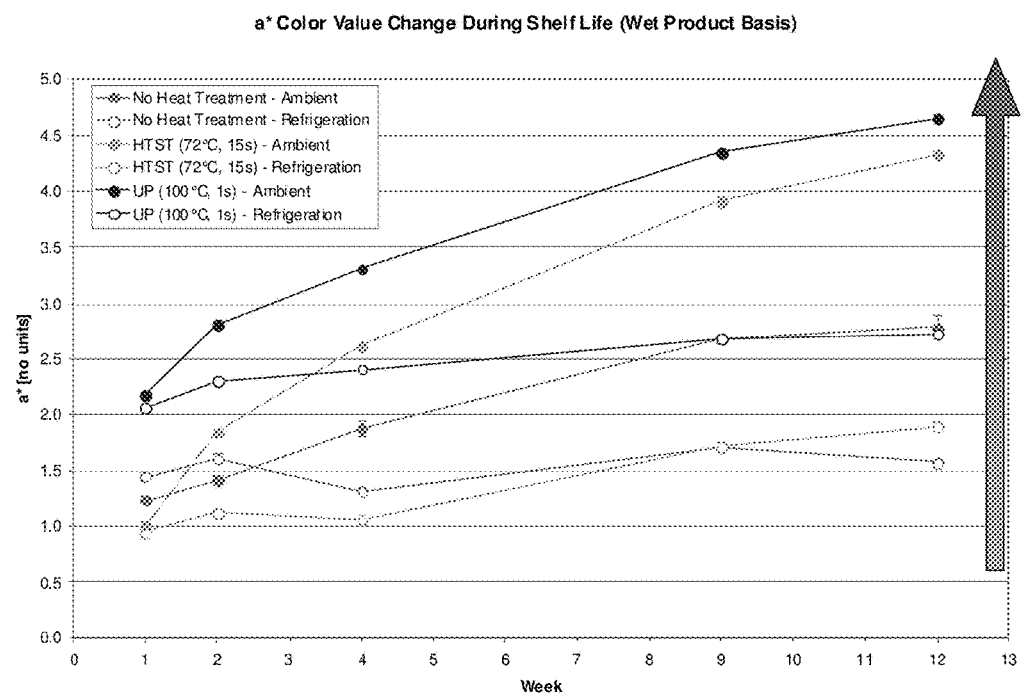
FIG. 6. Shows a* color value changes over time for Shelf Life Study #1.

From FIG. 6, one can see that the samples stored under refrigeration (open dots) generally had less browning than their ambient-stored counterparts (opaque dots). Further, by the end of the study, at a given storage condition, the order of browning was UP (most brown)>HTST>control (least brown). This indicates that the thermal treatments cause some browning in the OMPW and that this color difference is exacerbated over storage time. However, the absolute value of these differences is quite minimal. The a* scale goes from −60 to +60 on the instrument that was used for these measurements. So, at Week 12, the most brown samples differ from the most green samples by only 4 units out of 120.

Example 5

The following example illustrates time/temperature combinations for the thermal treatment of OMPW.

From November 2013 to February 2014, we performed a shelf-life experiment ("Shelf Life Study #2") testing 3 different thermal treatments (plus 1 control) and 2 storage conditions. The dependent variables of this experiment are summarized below.
Processing Methods
  No Heat Treatment (control)
  High Temperature Short Time (HTST: 72° C. for 15 seconds)
  Ultra Pasteurization (UP: 100° C. for 1 second)
  Ultra High Temperature Sterilization (UHT: 135° C. for 2 seconds)
  Storage Conditions
  Ambient (~20° C., laboratory room temperature)
  Refrigeration (2° C.)

As in Shelf Life Study #1, all samples were subjected to thermal treatment before homogenization. All samples in Shelf Life Study #2 were collected fresh from the olive mill on Nov. 18, 2013 and stored under refrigeration for less than 1 week before the Week 0 measurements were obtained. (These samples were never frozen.) Quality measurements were made at Weeks 0, 2, 4, 8, and 12. Microbiological measurements were performed by a contract analytical laboratory at Weeks 0, 4, 8, and 12. Findings from Shelf Life Study #2 were as follows:

Initial AOX of samples used in Shelf Life Study #2 (7500-9000 μmol Trolox/100 g OMPW) was higher than that of the samples used in Shelf Life Study #1 (5000-6000 μmol Trolox/100 g OMPW). The difference may have been due to differences in sample origin (OMPW collected in November 2011 for Shelf Life Study #1 vs. collected in November 2013 for Shelf Life Study #2) and/or storage condition (frozen/thawed for Shelf Life Study #1 vs. fresh for Shelf Life Study #2). Whatever the explanation, the samples for Shelf Life Study #2 started out at much higher AOX levels than did the samples for Shelf Life Study #1.

Figure 7:
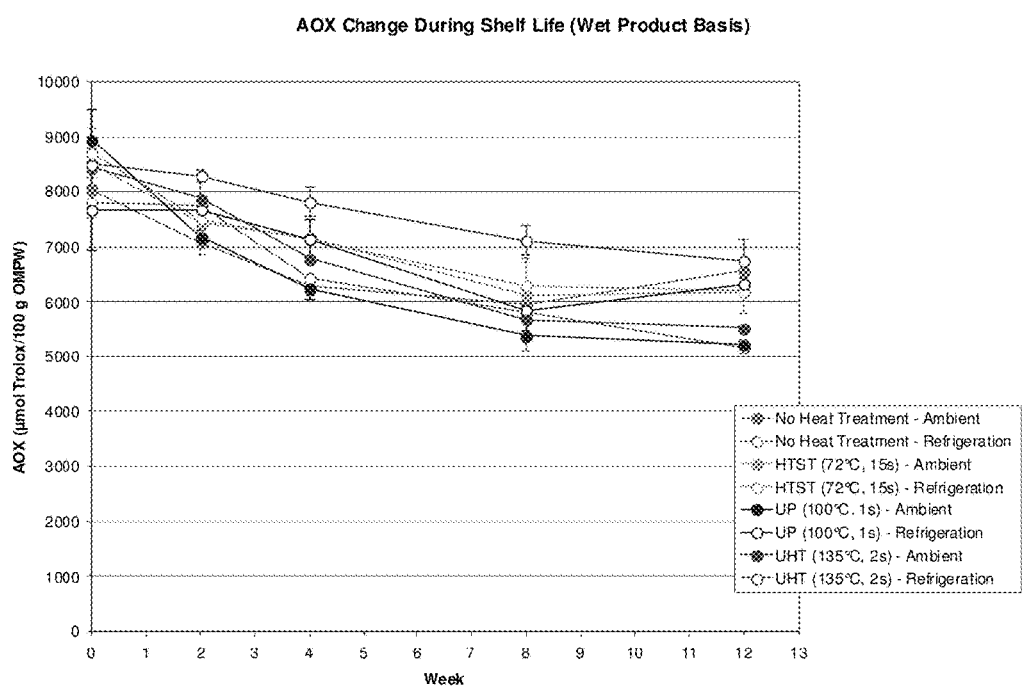
FIG. 7 Shows AOX changes over time for Shelf Life Study #2.

In contrast to the results from Shelf Life Study #1, all samples in Shelf Life Study #2 exhibited decreasing AOX over time. This is illustrated in FIG. 7. In FIG. 7, vertical brackets represent ±1 standard deviation of 3 replicate measurements for each data point.

In general, the refrigerated samples (open dots) fared better than their ambient-stored counterparts (opaque dots). The UHT samples stored under refrigeration had the highest AOX for all time points of the study, starting at Week 2.

The color results for Shelf Life Study #2 show a similar pattern to those of Shelf Life Study #1, in that the thermal treatments create some browning of the OMPW. However, the degree of browning was even less pronounced in Shelf Life Study #2, with the a* difference between the most green and the most brown samples being only 1.5 units out of a range of 120 units. It is unlikely that the human eye could discern such a subtle color difference.

The mold count results for Shelf Life Study #2 are summarized in Table 2. As expected, the (fresh, never frozen) control samples had a low but detectable mold count at Week 0. The control and HTST samples stored at ambient conditions saw a large spike in mold count at Week 8, though this level went down to below the limit of detection at Week 12. The results suggest that the UP and UHT treatments can control mold growth during ambient storage, and all 3 thermal treatments can control mold growth during refrigerated storage.

TABLE 2 mold counts for Shelf Life Study #2

| | Mold Count [cfu/g] | | | |
|---|---|---|---|---|
| | Week 0 | Week 4 | Week 8 | Week 12 |
| No Heat Treatment - Ambient | 30 | <10 | >570000 | <10 |
| No Heat Treatment - Refrigeration | 30 | 20 | <10 | <10 |
| HTST (72° C., 15 s) - Ambient | <10 | <10 | >570000 | <10 |
| HTST (72° C., 15 s) - Refrigeration | <10 | <10 | <10 | <10 |
| UP (100° C., 1 s) - Ambient | <10 | 40 | <10 | <10 |
| UP (100° C., 1 s) - Refrigeration | <10 | <10 | <10 | <10 |
| UHT (135° C., 2 s) - Ambient | <10 | 20 | <10 | <10 |
| UHT (135° C., 2 s) - Refrigeration | <10 | <10 | <10 | <10 |

Figure 8:
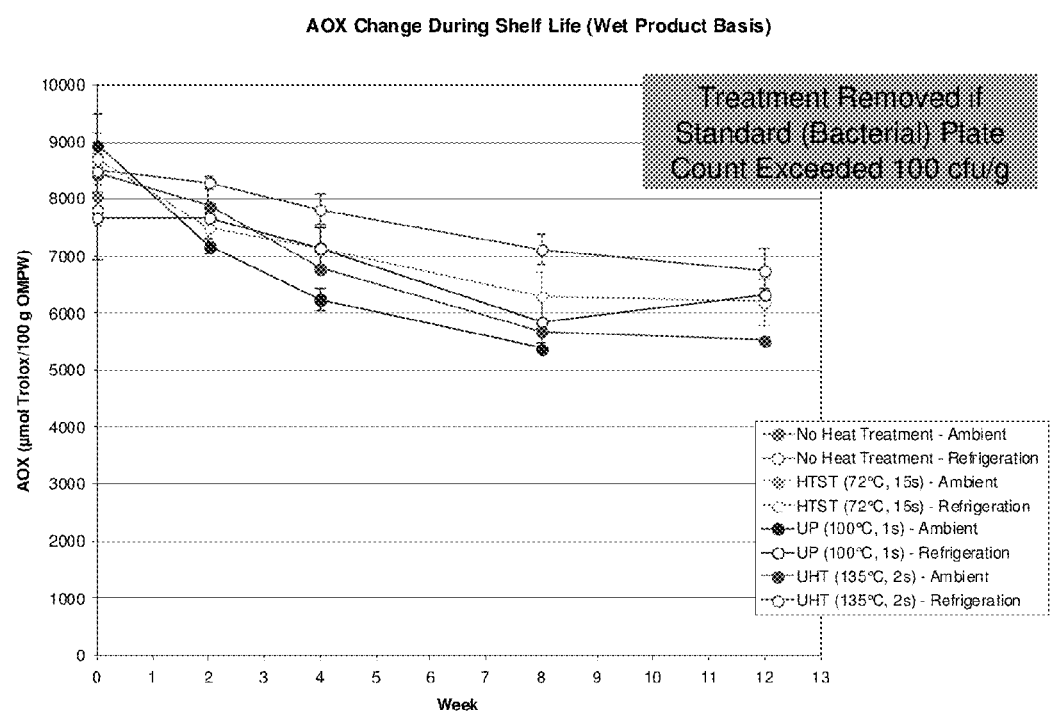
FIG. 8. AOX changes over time for Shelf Life Study #2; treatment removed from consideration when SPC first exceeded 100 cfu/g.
Figure 9:
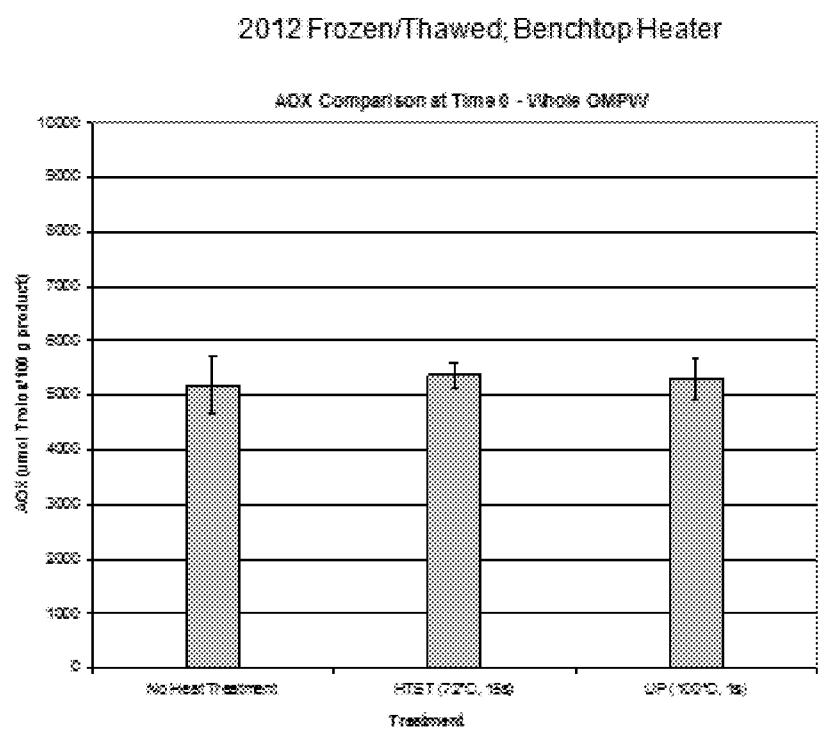
FIG. 9 is a graphical representation of relative antioxidant (AOX) levels of treated OMPW after thermal treatment.
Figure 10:
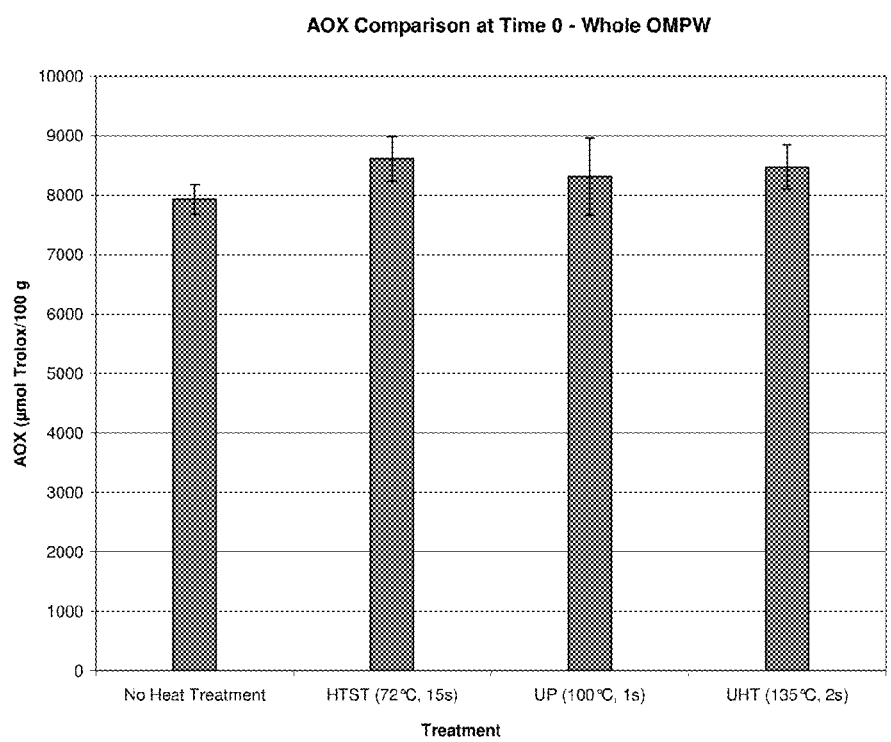
FIG. 10 is a graphical representation of relative antioxidant (AOX) levels of treated OMPW after thermal treatment.

It is instructive to view the SPC results combined with the AOX results, since OMPW with a high SPC would be unsuitable for use as a body care product ingredient, even if it had relatively high AOX. Thus, FIG. 8 depicts the same AOX results as FIG. 7, but samples are removed from the plot when their SPC first exceeds 100 cfu/g. From FIG. 8, one observes that only 4 treatments resulted in OMPW that was acceptable (from a microbiological standpoint) at Week 12 of the study. These treatments were the 3 tested thermal treatments under refrigerated storage, and the UHT treatment under ambient storage. This result demonstrates that thermally-treated OMPW remains suitable for inclusion in a body care product, even when stored at ambient conditions. The AOX of the UHT sample does decrease by about 35% over 12 weeks of ambient storage, but the AOX level appears to stabilize around Week 8.

Example 6

The following example illustrates the sensory and functional features of body care products in which the treated OMPW has been incorporated as a replacement for pure water (in whole and/or in part). This may include testing whether the antioxidant levels of the treated OMPW is sufficient to eliminate the need for the antioxidant ingredients that are currently added to body care products.

In late May 2013, bar soaps were prepared containing OMPW replacing 0%, 25%, 50%, 75%, and 100% of the water that is normally used for bar soap production. We observed that any OMPW level above 25% made the soap brown. Thus, new lines of body care products for which the brown color is desirable are created using 25% or more thermally treated OMPW.

Example 7

The following example illustrates an exemplary process by which the AOX of OMPW was increased by both a heat treatment and a sequence of heat treatment and homogenization, and this increase was maintained in the heat-treated material during 12 weeks of both ambient-temperature and refrigerated storage.

OMPW was prepared according to the methods of Example 3, with the exception that the frozen OMPW was stored at −20° C. for 5 months (vs. 3 months in Example 3). The target heat treatment temperatures and times were as follows: 72° C. for 15 seconds, 100° C. for 3 seconds, and 138° C. for 3 seconds. In this Example, the heat treatments were applied to OMPW as it was circulated through a pilot-scale, electrically-heated pasteurization system (MicroThermics E-Series EHVH). This system heats the sample to a setpoint temperature, pumps the sample through a holding section for a set amount of time, and then cools the sample to room temperature (ca. 20° C.). Homogenization was performed on the samples after they exited the pasteurization system. The "No Treatment" sample did not receive any heat treatment but was homogenized in the same way as the 72° C., 100° C., and 138° C. samples.

AOX was measured the same day that the heat treatment and homogenization were performed as well as 2, 4, 8, and 12 weeks after that day. Treated samples were either held at 2° C. ("Refrigeration") or ca. 20° C. ("Ambient") between AOX measurements.

Figure 11:
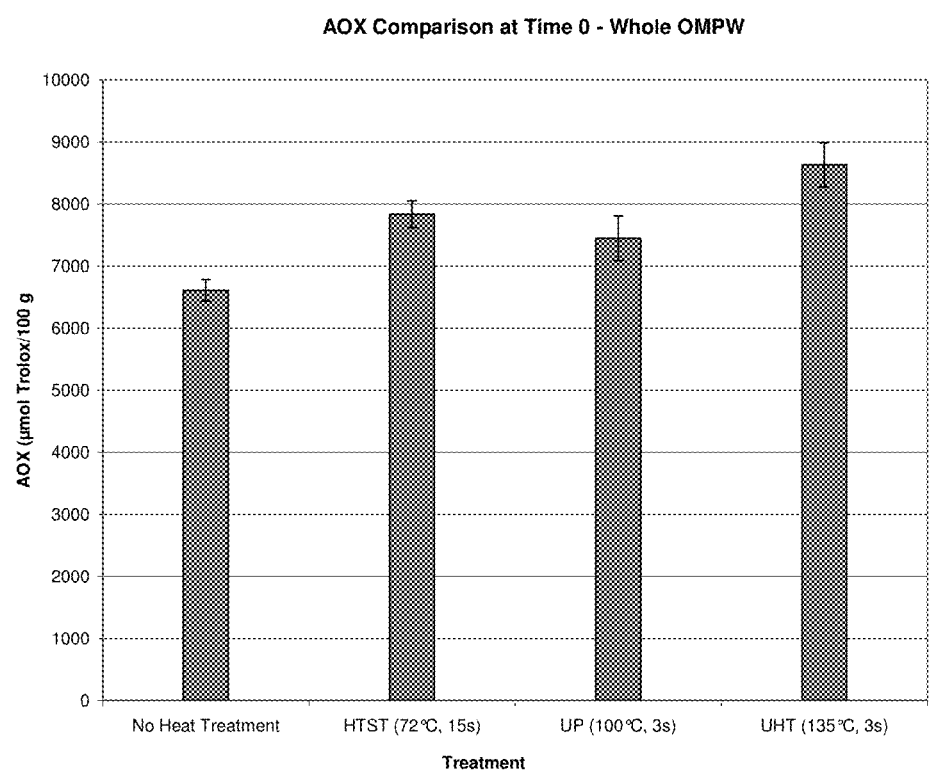
FIG. 11 is a graphical representation of relative antioxidant (AOX) levels of treated OMPW after thermal treatment.
Figure 12:
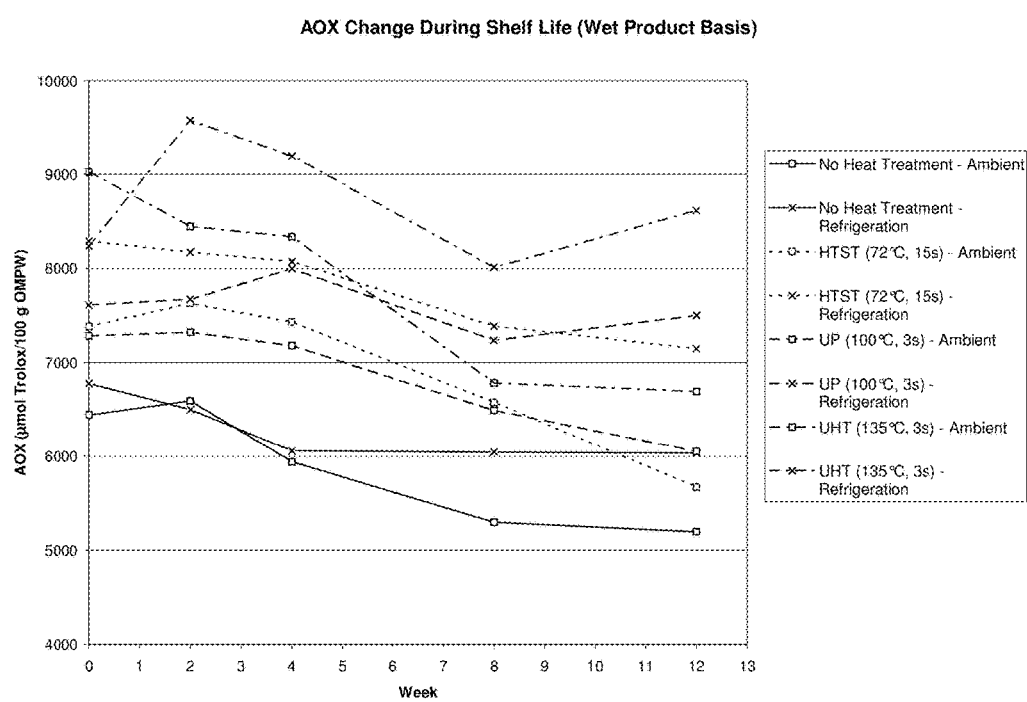
FIG. 12 illustrates the relative antioxidant (AOX) levels of treated OMPW after thermal treatment through 12 weeks of storage.

The results of these procedures are shown in FIGS. 11-12. In FIGS. 11-12, vertical brackets represent ±1 standard deviation of 3 replicate measurements for each data point. At Week 0 (i.e. immediately after heat treatment and homogenization), the 72° C., 100° C., and 138° C. samples exhibited AOX increases of 18.5%, 12.7%, and 30.6%, respectively, over the No Treatment sample. This is depicted in FIG. 11. With some minor fluctuations, the relative AOX levels among the samples persisted through 12 weeks of storage. This is depicted in FIG. 12.

Example 8

The following example illustrates the sensory and functional features of body care products in which the treated OMPW has been incorporated.

A panel of 17 users of liquid skin care products conducted an assessment of 3 potential toner products: water, 5% treated OMPW/95% water ("5%" hereafter), and 20% treated OMPW/80% water ("20%" hereafter). Samples were coded with random 3-digit numbers and presented in tinted spray bottles, so panelists did not know the composition of the samples. The panelists rated the 5% samples as lower in the undesirable attributes of "Residue" and "Stickiness" than both the water and 20% samples. Furthermore, the panelists rated the 5% samples as no different than water in terms of the attributes of "Pigmenting", "Absorption", "Moisturization", and "Freshness". Thus, in an exemplary embodiment, a formulation of 5% treated OMPW/95% water is used as a sensorially-acceptable liquid skin care product.

Example 9

The following example illustrates an exemplary fluid food product in which the treated OMPW has been incorporated.

Agitate 3 parts vinegar (such as red wine vinegar or white wine vinegar) with 1 part of treated OMPW. Dry seasonings such as salt and pepper may be added to this mixture. Gradually add in 24 parts vegetable oil and agitate to combine.

This is a prophetic example.

Example 10

The following example illustrates an exemplary beverage product in which the treated OMPW has been incorporated.

Combine 4 parts treated OMPW, 3 parts orange juice, 4 parts sucrose, 7 parts coconut milk, 12 parts apple juice, 28 parts banana puree, and 42 parts pineapple juice. Blend the mixture for 3 minutes. Optionally, process the mixture at for 5 min at 6400 rpm in a high shear mixer. Optionally, filter the mixture through an emulsor screen.

This is a prophetic example.

Example 11

The following Example illustrates preparation of glycerin bar soaps which comprise treated OMPW as disclosed herein.

General Protocol for Mixing Ingredients

1) The lye solution is prepared by weighing out the water and then adding the sodium hydroxide to the water and stirring until completely mixed. The resulting solution is allowed to cool until the temperature of the solution is between about 135° F. to 145° F.

2) Heat the oils. The oils e.g., coconut, castor, palm, jojoba, olive, and calendula oils are weighed out into a pot. The oils are then heated until the temperature reaches 135° F. to 145° F.

3) Once the lye solution and the oils are between 135° F. to 145° F., the lye solution from step 1 is added to the oils and stirred (e.g., with a stick blender or a whisk). Stirring is continued until the soap reaches trace. If the temperature drops much below 135° F., the solution is reheated, typically over medium, low heat, and stirring is continued until the soap reaches trace.

4) After reaching trace, the soap is covered and allowed to sit. In an exemplary embodiment, the lid is placed over the pot and covered with a blanket. The covered pot is allowed to sit until gelled, typically for at least about 1 hour.

5) Stir and Recover. After sitting a sufficient time to gel, the pot is uncovered and the gelled soap is stirred briefly, e.g., for a minute or so, paying attention to scrape away the harder soap from the sides of the pot. After stirring the soap to mix to homogeneity by making sure to get the harder soap mixed in with the hotter soap in the middle, the pot is again covered and the gelled soap is again allowed to sit and gel further typically for about 1 hour.

6) Uncover pot and add the alcohol and glycerin. The soap should still be hot and in a gel state. Once added stir to mix thoroughly.

7) While stirring in the glycerin and alcohol care is taken to scrape the bottom and sides of the pot to prevent the soap from burning. Chunks that form are broken up to keep the mixture homogenous.

8) When the mixture is homogeneous and thus, stirring is complete, cover the top of the pot with plastic and tie the plastic around the top e.g., with a rope.

9) Place the covered pot into a double boiler. Bring the soap solution to a gentle boil and then reduce heat to maintain the boil. Cook the soap solution for roughly 30 minutes.

10) After 30 minutes of cooking the soap, prepare the sugar solution. In a separate pan, bring the water portion of the sugar solution to a boil and then add the sugar. Stir the sugar solution until completely dissolved. Cover the solution, bring back to a boil and let simmer briefly e.g., for 2 to 3 minutes. Uncover the plastic from the soap solution and add the sugar solution to the soap.

11) Cover pot with a lid and blanket for roughly 20 minutes or until temperature of the soap drops to 140° F.

12) Uncover the pot and add the fragrance or essential oils. Stir until mixed.

13) Pour soap into lined mold.

14) Allow the soap to harden typically for about a day.

15) Cut soap.

16) Let soap cure for at least 2 weeks.

Specific Glycerin Soap Formulations:

Formula A
   Coconut oil 14.32%
   Castor Oil 13.79%
   Palm Oil 13.79%
   Ethanol 14.85%
   Glycerin 4.24%
   Treated Olive Mill Process Water 13.26%
   Sodium Hydroxide 6.37%
   Water 7.96%
   Sugar 10.61%
   Patchouli 0.74%
   Tea Tree 0.05%

Formula B
   Coconut oil 13.53%
   Castor Oil 13.03%
   Palm Oil 13.03%
   Ethanol 15.04%
   Glycerin 10.03%
   Treated Olive Mill Process Water 12.53%
   Sodium Hydroxide 6.02%
   Water 6.52%
   Sugar 9.52%
   Patchouli 0.70%
   Tea Tree 0.05%

Formula C

| Ingredient | Percentage |
| --- | --- |
| Coconut oil | 7.57% |
| Castor Oil | 5.05% |
| Palm Oil | 11.10% |
| Jojoba Oil | .08% |
| Olive Oil | 5.05% |
| Calendula Infused Olive Oil | 4.04% |
| Vitamin E | 0.20% |
| Ethanol | 14.64% |
| Glycerin | 7.57% |
| Treated Olive Mill Process Water | 6.31% |
| Sodium Hydroxide | 6.06% |
| Water | 12.87% |
| Sugar | 9.08% |
| Geranium Essential Oil | 1.26% |
| Lavandin Grosso Essential Oil | 0.64% |
| Ylang Ylang Essential Oil | 0.39% |
| Extract Blend | 0.10% |

Example 12

The following Example illustrates preparation of personal care skin care products which comprise treated olive mill process water (OMPW) as disclosed herein.

Antioxidant Toner
   1.0 oz distilled water
   0.8 oz aloe vera juice
   0.75 oz rose hydrosol
   0.6 oz citrus aurantium (orange distillate)
   0.4 oz witch hazel
   0.2 oz calendula glycerite
   0.2 oz treated OMPW
   0.05 oz tocopheryl acetate (vitamin E)

Cleansing Toner
   1.0 oz distilled water
   0.8 oz aloe vera juice
   0.75 oz witch hazel
   0.75 oz rose hydrosol
   0.25 oz. alcohol
   0.2 oz calendula glycerite 0.2 oz treated OMPW 0.05 oz tocopheryl acetate (vitamin E)

In toner formulations, OMPW is typically present in a concentration that is between about 3% to about 7%. In the above formulations, water can be substituted with a botanical hydrosol or herbal infusion. Other actives such as Cranberry, Raspberry Seed Oil, Seabuckthorn Oil can be added. Vitamin E can be substituted or combined with other preservatives such as sodium benzoate, potassium sorbate, ethyl hexyl glycerin.

Toner is typically formulated so that it does not leave brown residue on skin and has a pH range of 4.0 to 5.5. Toner is typically formulated to keep product preserved for at least one year. To make, all ingredients are mixed together.

Serum 5.29 oz herbal infusions 4.75 oz distilled water 4.25 oz. aloe vera 2.65 oz glycerin 1.06 oz treated OMPW 0.2 oz carrageen 1.0 oz olive oil 1.0 oz avocado oil 1.0 oz carrot seed oil 0.1 oz evening primrose) oil 0.1 oz neem seed oil 60 drops Vitamin E 50 drops of rose geranium essential oil 30 drops rosemary oleoresin extract or sodium benzoate 20 drops of potassium sorbate 10 drops ethyl hexyl glycerin Exemplary serum products comprising e.g., the ingredients listed above, are made by slowly mixing carrageen into warmed distilled water to prepare a first solution. Separately mix aloe vera, OMPW, and hydrosols with glycerin to prepare a second solution. Pour the second solution into the first solution and mix thoroughly. Mix in essential oils, then olive oil and palm oil, and then vitamin E and any other preservatives.

In some exemplary embodiments, glycerin is substituted or used in combination with glycerites and/or used in combination with powdered extracts. Various essential oils or fragrances or a combination of essential oils and/or fragrances can be used instead of or in combination with rose geranium essential oil. OMPW is typically present in a concentration that is between about 3-about 7%. In some exemplary embodiments, water is substituted with an herbal infusion or botanical hydrosol. Vitamin E can be substituted or combined with other preservatives such as sodium benzoate, potassium sorbate, ethyl hexyl glycerin.

Serum is typically formulated so that it does not leave brown residue on skin and has a pH range of 4.0 to 5.5. Serum formulation disclosed herein above should keep product preserved for at least one year.

Vitamin E can be used in combination with or can be substituted with other vitamins such as Retinyl Pamitate (Vitamin A), Niacinamide (Vitamin B3), Ascorbyl Palmitate (Vitamin C Ester).

Cream 5.0 oz distilled water 5.0 oz lavender hydrosol 3.5 oz aloe vera 1.2 oz glyceral stearate 1.0 oz. OMPW 1.0 oz squalene 1.0 oz olive oil 1.0 oz palm oil 1.0 oz( carrot) seed oil 0.3 oz combination of propylene glycol, diazolidinyl urea and iodoprpynyl butylcarbamate 0.2 oz essential oil and/or fragrance Created using industry standard method see e.g., M. L. Schlossman (2009) Chemistry and Manufacture of Cosmetics: Volume II—Formulating, 4th Edition, Allured Pub Corp; Anthony Dweck (2010) Formulating Natural Cosmetics, Allured Pub Corp; André O. Barel, Marc Paye, and Howard I. Maibach (2014) Handbook of Cosmetic Science and Technology, CRC Press; S. K. Singh (2010) Handbook on Cosmetics (Processes, Formulae with Testing Methods) Asia, Pacific Business Press Inc.

Preparation includes standard oil phase, emulsifier water phase, anti-oxidants and preservatives, and essential oils or fragrance.

Glyceral stearate can be substituted with or used in combination with other waxes such as beeswax, carnauba wax, emulsifying wax NF, cetearyl alcohol, olive wax, and/or polysorbate 20.

Lotion should be formulated to a pH of 6-6.5. OMPW is present in the range of 3-about 7%. All other substitutions listed above can be used here.

In all of the disclosed examples disclosed, water can be distilled, deionized, or spring water.

Face Mask 30.0 oz clay 24.0 oz aloe vera juice 15.0 oz water 10.0 oz treated OMPW 4.0 oz glycolic acid 3.0 oz. squalene 2.0 oz. lactic Acid 2.0 oz. glycerin 1.0 oz. sweet almond oil 1.0 oz. grapeseed oil 1.0 oz. olive oil 0.5 oz. seabuckthorn oil 0.5 oz. rose hip oil 1.0 oz. jojoba oil 1.0 oz. apricot kernel oil 0.9 oz tocopherol 1.0 oz oregon grape extract 1.0 oz green tea leaf powder 1.0 oz. licorice extract 1.0 oz. bayberry extract 1.0 oz. grapefruit essential oil 1.0 oz. clove bud essential oil 0.8 oz potassium sorbate 0.8 oz xanthan gum 0.8 oz phenoxyethanol 0.7 oz benzyl alcohol Combine all ingredients besides preservatives to make a smooth paste by mixing for approximately 30 minutes using a high-shear mixer at approximately 8,000 rev/min. Add humectants in sequence after hydrating with water. Adjust to desired thickness by varying the amount of oil, aloe vera, or water. Mask should be formulated to a pH of 5.4-6.5. Clay is not limited to the following clays or a combination of the following clays: Red Clay, Green Clay, Obsidian Clay, and Kaolin Clay. Muds can also be used in substitution or in combination with these clays. Treated OMPW is present in concentrations of 3-25%. All other substitutions listed in prophetic examples above can be used here.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for preparing treated olive mill process water (treated OMPW) from Olive mill process water (OMPW), wherein the treated OMPW has increased antioxidant levels by comparison to the OMPW, the method steps consisting of:
   (i) ramping up temperature of the OMPW from a starting temperature to a target temperature, wherein the target temperature is in a range that is between about 70° C. and about 138° C.;
   (ii) holding the OMPW at the target temperature, for a target time, and
   (iii) actively cooling the OMPW to room temperature, thereby preparing treated OMPW from OMPW wherein the treated OMPW has increased antioxidant levels by comparison to the OMPW
   (iv) optionally homogenizing the treated OMPW.

2. The method of claim 1, wherein the antioxidant levels of the treated OMPW is increased by at least about 5% by comparison to the untreated OMPW.

3. The method of claim 1 wherein, in step (ii), the target time is 1-15 seconds.

* * * * *